United States Patent [19]

Goel et al.

[11] 4,456,555
[45] Jun. 26, 1984

[54] MANUFACTURE OF ARYL ESTERS

[75] Inventors: Anil B. Goel, Worthington; Robert A. Grimm, Columbus, both of Ohio

[73] Assignee: Ashland Oil, Inc., Ashland, Ky.

[21] Appl. No.: 416,810

[22] Filed: Sep. 13, 1982

[51] Int. Cl.$^3$ .......................... C11C 3/02; C09F 5/08
[52] U.S. Cl. .................................. 260/410; 260/410.5; 260/406
[58] Field of Search ................ 260/410 R, 406, 410.5; 560/131

[56] References Cited

U.S. PATENT DOCUMENTS

| | | | |
|---|---|---|---|
| 3,493,605 | 2/1970 | Selwitz | 260/410.5 |
| 3,646,111 | 2/1972 | Hörnig et al. | 560/131 |
| 3,651,127 | 3/1972 | Hörnig et al. | 560/131 |
| 3,772,383 | 11/1973 | Kominami et al. | 560/131 |
| 4,229,587 | 10/1980 | Murib | 560/131 |

*Primary Examiner*—Y. Harris-Smith
*Attorney, Agent, or Firm*—John F. Jones

[57] ABSTRACT

A process is described for the manufacture of aryl esters such as phenyl esters by liquid phase reaction of an aromatic compound such as benzene with molecular oxygen in the presence of a perfluorocarboxylic acid and carboxylic acid preferably having 5 or more carbon atoms over a catalyst composed essentially of a compound of palladium, an antimony compound and optionally a compound of at least one member selected from the group consisting of chromium, cobalt, nickel, manganese, iron and tin wherein the aromatic compound is added continuously to the reaction and water formed in the reaction is rapidly and continuously removed from the reaction mixture.

11 Claims, No Drawings

MANUFACTURE OF ARYL ESTERS

CROSS-REFERENCE TO RELATED APPLICATIONS

This invention is an improvement over the process more fully described and claimed in the copending U.S. patent application Ser. No. 348,561, filed Feb. 12, 1982 by Anil B. Goel and Robert A. Grimm. Improved Catalysts are more completely described in the copending U.S. patent application Ser. No. 441,360, filed Oct. 15, 1982 by Anil B. Goel and Peter E. Throckmorton.

BACKGROUND OF THE INVENTION

1. Field of the Invention

The present invention provides a process for making phenolic esters, and if desired, phenols from aromatic compounds, such as benzene, naphthalene, phenanthrene, anthracene, biphenyl, terphenyls, etc., which comprises reacting a mixture of the aromatic compound, for instance benzene, a carboxylic acid, preferably having at least 5 carbon atoms, a perfluorocarboxylic acid, and molecular oxygen in the liquid phase in the presence of a catalyst composed of palladium or a compound of palladium, a compound of antimony, and optionally a compound of at least one member selected from the group consisting of chromium, cobalt, nickel, manganese, iron and tin.

2. Description of the Prior Art

The manufacture of phenol by direct oxidation of benzene with oxygen is known. There are, for instance, thermal processes which are performed at very high temperatures in which the phenol formed is susceptible to further oxidation so tht considerable loss of yield occurs as disclosed in U.S. Pat. No. 2,223,383. In the presence of catalysts, the oxidation can be carried out at somewhat lower temperatures as in U.S. Pat. No. 3,133,122, but the reactions have been plagued by low conversions and excessive production of unwanted by-products as disclosed in U.S. Pat. No. 2,392,875.

It has been proposed to make phenyl acetate and biphenyl from benzene and acetic acid in the liquid phase in the presence of palladium acetate and without added molecular oxygen by a stoichiometric reaction in *Chem. and Ind.*, Mar. 12, 1966, Page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently this preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc., are disadvantageous for an industrial process. U.S. Pat. No. 3,772,383 describes a liquid phase reaction using a very complex catalyst system which includes the use of nitric acid and a lower aliphatic carboxylic acid such as acetic, propionic, n-butyric, isobutyric or caproic acid. Generally speaking, these prior art processes deal for the most part with vapor phase oxidation reactions, or liquid phase reactions in which all the reactants (except oxygen in some instances) are initially included in the reaction mixture, they use lower aliphatic carboxylic acids such as acetic acid and propionic acid, and they often require an alkali or alkaline earth metal carboxylate as part of the catalyst. Morever, in general the prior art catalytic processes have produced very low conversions, usually less than 10%, with poor selectivity to the desired phenyl ester, and phenol is often a primary product. The use of the lower saturated aliphatic carboxylic acids, primarily acetic acid, in the prior art processes produce a highly corrosive system which can cause reaction equipment problems and excessive recycle costs as well as the poor conversions and selectivities mentioned above. None of the prior art processes disclose the continuous addition and removal of benzene and continuous removal of water from the reaction mixture as it forms. The prior art does not disclose the use of any perfluorocarboxylic acid in the aromatic hydrocarbon oxidation process.

SUMMARY OF THE INVENTION

We have discovered an oxidation process for the transformation of benzene, and similar aromatic compounds, molecular oxygen and a carboxylic acid to the corresponding aromatic carboxylate in high conversions and selectivities to the desired product. Our discovery is based to some extent upon the use of relatively higher boiling mono or poly-carboxylic acid such as lauric acid or dodecanedioic acid as the carboxylic reactant and the inclusion of a perfluorocarboxylic acid in our process. The use of carboxylic acids having 5 or more carbon atoms and a liquid phase in our process and the inclusion of a perfluoro carboxylic acid as well as the use of our palladium-antimony type catalyst not only helps in dramatically increasing the conversion of benzene and increasing the selectivity to the phenyl carboxylate over that described in the prior art, but these carboxylic acids are much less corrosive and much easier to recycle than are the lower aliphatic carboxylic acids disclosed for similar types of reactions in this prior art. The perfluoro carboxylic acids used in this improved process can also be readily recycled.

The perfluorocarboxylic acids useful in this process are those having the formula $C_nF_{2n+1}COOH$ wherein n is 1–13 and such acids include trifluoroacetic acid, perfluorobutyric acid, perfluorooctanoic acid, perfluorododecanedioic acid, and the like.

The liquid phase reaction of this invention produces high conversions and quantitiative yields of phenyl ester when benzene is continuously added to and water is removed from the reaction mixture during the entire course of the reaction. Excess amounts of benzene in the reaction mixture during the oxidation reaction appear to be responsible for the production of undesirable by-products such as biphenyl. Water formed in the reaction is conveniently removed by entrainment with benzene as some of the benzene is continuously removed by distillation during the entire course of the reaction. If water, which is a by-product of the oxidation reaction, is allowed to remain in the reaction mixture it causes hydrolysis of the phenyl ester to form phenol which can cause fouling and inactivation of the catalyst.

The catalysts of our process are preferably composed of palladium metal or compounds of palladium and usually a palladium carboxylate in conjunction with an antimony compound which can also be a carboxylate for convenience and optionally a compound of at least one member selected from the group consisting of chromium, cobalt, nickel, manganese, iron and tin. The catalysts of this invention may be used alone or may be supported on a carrier or carriers. Suitable carriers include silica, alumina, carbon, quartz, pumice, diatomaceous earth, and the like and others which are known in the art of catalysis.

The carboxylic acids useful in invention include mono and poly-carboxylic acids and preferably those having 5 or more carbon atoms which correspond to the formula $R(COOH)_n$ wherein n is an integer of 1 or more and R is a hydrocarbon having at least 5-n carbon atoms, some carboxylic acid anhydride can be included with the carboxylic acid if desired.

Our liquid phase oxidation process produces in the case of benzene reactant conversions of the carboxylic acid in the order of 10% or greater with selectivities to the phenyl ester in the order of 100%. Thus, our process produces product in such significant quantities that it is directly competitive with the best of the present day commercial processes for the manufacture of phenyl esters and ultimately phenol itself. The phenyl ester or phenyl carboxylate product of our process can be converted to phenol and the corresponding carboxylic acid by known methods for hydrolysis or pyrolysis. The phenol is readily recovered by known means and the carboxylic acid, ketone or acid anhydride is readily recycled for further use in the oxidation reaction of this invention.

DESCRIPTION OF THE PREFERRED EMBODIMENT

In a typical reaction in accordance with this invention a mixture of benzene and the carboxylic acid including a perfluorocarboxylic acid is contacted with the catalyst in an oxygen containing atmosphere at a reaction temperature in the range of from about 100° to 300° C. and preferably from 140° to 200° C., and at from 1 to 100, preferably from about 1 to 10 atmospheres but most preferably at or near atmospheric pressure. This molecular oxygen can be oxygen, per se, or any gaseous mixture containing molecular oxygen. For instance, molecular oxygen can be in the form of air for convenience. The catalyst can be a mixture of $(CH_3COO)_2Pd$ and $(CH_3COO)_3Sb$, for instance, in molar ratio of about 1:1. This molar ratio of Pd:Sb can vary within the range of from 10:1 to 1:20 and preferably 1:0.1 to 1:10. The molar ratio of optional metal compound to Pd/Sb can vary from 0:1 to 20:1. The molar ratio of perfluorocarboxylic acid to the $R(COOH)_n$ reactant in this process is in the range of from 0.01 to 100 and preferably from 0.1 to 10. During the reaction the water formed can be continuously removed by azeotropic distillation with benzene which is continuously added to the reactor during the course of the reaction. The major product (and in most cases the only product except for traces of $CO_2$), the phenyl carboxylate obtained by the process of this invention, far exceeds the best yields reported in the prior art with essentially quantitative selectivity. As previously mentioned, the phenyl carboxylate thus obtained can be hydrolyzed if so desired to produce phenol by known means and the carboxylic acid, perfluorocarboxylic acid and catalyst can be recycled back into the oxidation reaction.

Because essentially no phenol is produced in the process of this invention, it is believed that catalyst activity is maintained for long periods of time under continuous use. The rapid removal of water from the reaction mixture is probably at least partly responsible for the absence of phenol in the reaction product. The presence of phenol in the reactor is believed to be responsible for catalyst fouling and short catalyst life which has been minimized in our process. The process of this invention is further demonstrated in the following illustrative examples.

EXAMPLE 1

Into a 250 ml. 3 necked flask equipped with a mechanical stirrer, reflux condenser and Dean-Stark tube, was charged with 1.35 g. of palladium (II) acetate (0.006 mol), 1.8 g of antimony (III) acetate (0.006 mol), 66 g. of lauric acid (0.33 mol), 3 g. (0.026 mol) of trifluoroacetic acid and 5 ml. of benzene. The resulting mixture was stirred and heated at 163° C. and oxygen was bubbled through the reaction mixture at a flow rate of about 50 cc/min. Water formed during the reaction and it was removed continuously as it formed azeotropically with excess benzene. The temperature was held at $163\pm3°$ C. During the course of the reaction additional benzene was fed to the reaction mixture by pump. The reaction was carried out for a period of 5 hours during which time about 3 ml. of water was produced and the total benzene fed was 0.21 mols. GLC analysis of the reaction mixture after 5.0 hours reaction time showed that the phenyl ester of lauric acid was formed (44 millimols, 14% conversion of the lauric acid) with a selectivity of about 100% to the phenyl ester. Only a trace of $CO_2$ and no biphenyl were detected in the reaction.

EXAMPLE 2

In this example which is included for comparison purposes and is outside the scope of the present invention the procedure of Example 1 was repeated except that 0.277 mol of lauric acid was used in place of that used in Example 1 and no trifluoroacetic acid was used. Analysis of the reaction mixture at the end of a 6 hour reaction period showed that 10% of the lauric acid was converted to the phenyl ester (28 millimols) with nearly 100% selectivity.

EXAMPLE 3

The procedure of Example 1 was repeated except that 28 millimols of trifluoroacetic acid were used, 0.54 mol of benzene was introduced into the reactor continuously during the reaction time, the reaction temperature was 168° C. and the reaction time was 14 hours. Analysis of the final reaction mixture showed that 98 millimols (30% conversion) of lauric acid were converted and that the selectivity was 99% (a trace of $CO_2$ was observed) to phenyl laurate.

EXAMPLE 4

The procedure of Example 1 was repeated except that 24 millimols of perfluorobutyric acid were used in place of the perfluoroacetic acid, 0.13 mol of benzene was introduced into the reactor, and the reaction temperature was 165° C. At the end of the 5 hour reaction period analysis showed that 38 millimols (12% conversion) of lauric acid were converted with a selectivity of 98% to phenyl laurate.

EXAMPLE 5

The procedure of Example 1 was repeated except that 4 millimols of perfluorooctanoic acid were used in place of the trifluoroacetic acid, 0.22 mol of benzene was introduced in the reactor, and the reaction temperature was 165° C. At the end of the 5 hour reaction period analysis of the product showed that 42 millimols (13% conversion) of lauric acid were converted with a selectivity of 99% to phenyl laurate.

EXAMPLE 6

The procedure of Example 1 was repeated except that 6 millimols of perfluorodecanoic acid were used in place of the trofluoroacetic acid, 0.16 mol of benzene was added during the reaction period to the reactor, a reaction temperature of 160° C. and a reaction time of 7 hours were used. Analysis of the product showed that 38 millimols (12% conversion) of lauric acid were converted with a selectivity of 98% to phenyl laurate.

EXAMPLE 7

The procedure of Example 1 was repeated except that 15 millimols of trifluoroacetic acid were used, 0.73 mol of benzene was continuously added during the reaction period into the reactor, the reaction temperature was 167° C. and the reaction time was 9 hours. Analysis of the resulting reaction product showed that 52 millimols (16% conversion) of lauric acid were converted with a selectivity of 99% to phenyl laurate.

EXAMPLE 8

The procedure of Example 1 was repeated except that 8 millimols of perfluorooctanoic acid were used in place of the trifluoroacetic acid, 264 millimols of lauric acid were used, a total of 0.24 mol of benzene was used and a reaction time of 5.1 hours was employed. The analysis of the product showed that 36 millimols (13% conversion) of the lauric acid was converted with a selectivity of 98% to the phenyl ester.

EXAMPLE 9

The reactor was charged with 3.75 g. (29 m moles) of naphthalene, 47.6 g. (333 m moles) of octanoic acid, 1.36 g. (6 m moles) of Pd(OAc)$_2$, 1.80 g. (6 m moles) of Sb(OAc)$_3$ and 12 m moles of trifluoroacetic acid. Benzene (11.3 g., 144 m moles) was continuously added and removed by distillation during the reaction. The reaction was carried out with stirring at 160±5° C. with a constant flow of oxygen through the reaction mixture of 50 cc/minute. After a reaction time of 5 hours GLC analysis of the reaction mixture showed that 100% of the naphthlene charged was converted to naphthyl ester (93% alpha, 7% beta-naphthyl octanoate) and 14 m moles of the benzene was converted to phenyl octanoate.

We claim:

1. An oxidation process for the manufacture of aryl esters comprising contacting a reaction mixture of an aromatic compound, a carboxylic acid, a perfluorocarboxylic acid and molecular oxygen in the liquid phase at a temperature in the range of 100° to 300° C. with a catalyst comprising palladium carboxylate or a carboxylate of palladium and an antimony carboxylate.

2. The process of claim 1 wherein the carboxylic acid has the formula R(COOH)$_n$ wherein n is an integer of one or more and R is a hydrocarbon group having at least 5-n carbon atoms, the perfluoro carboxylic acid is one having the formula $C_nF_{2n+1}COOH$ wherein n is from 1-3. The aromatic compound is added continuously to the reaction mixture, and the water formed in the process is removed continuously from the reaction mixture as the aryl ester is formed.

3. The process of claim 2 wherein the aromatic compound is benzene.

4. The process of claim 2 wherein the carboxylic acid is dodecanedioic acid.

5. The process of claim 2 wherein the carboxylic acid is lauric acid.

6. The process of claim 2 wherein the perfluorocarboxylic acid is trifluoroacetic acid.

7. The process of claim 2 wherein the perfluorocarboxylic acid is perfluorobutyric acid.

8. The process of claim 2 wherein the perfluorocarboxylic acid is perfluorooctanoic acid.

9. The process of claim 2 wherein the perfluorocarboxylic acid is perfluorodecanoic acid.

10. The process of claim 2 wherein the aromatic compound is naphthalene.

11. The process of claim 2 wherein the carboxylic acid is octanoic acid.

* * * * *